(12) United States Patent
Kert

(10) Patent No.: US 8,092,216 B2
(45) Date of Patent: Jan. 10, 2012

(54) HANDSET AND OPTICAL TIP FOR PHOTOSYNTHESIS

(75) Inventor: Jimmie Kert, Monaco (MC)

(73) Assignee: CMS Dental APS, Copenhagen (DK)

( * ) Notice: Subject to any disclaimer, the term of this patent is extended or adjusted under 35 U.S.C. 154(b) by 43 days.

(21) Appl. No.: 12/257,050

(22) Filed: Oct. 23, 2008

(65) Prior Publication Data

US 2009/0047618 A1    Feb. 19, 2009

Related U.S. Application Data

(63) Continuation-in-part of application No. 11/694,475, filed on Mar. 30, 2007.

(51) Int. Cl.
*A61C 1/00* (2006.01)
*A61C 5/02* (2006.01)

(52) U.S. Cl. ............ 433/29; 433/224; 433/118; 433/165

(58) Field of Classification Search .................. 433/102, 433/80, 215–229, 29–31, 141, 118–119, 433/165; 385/43; 606/2–19; 362/612–620; 607/88–94

See application file for complete search history.

(56) References Cited

U.S. PATENT DOCUMENTS

| | | | |
|---|---|---|---|
| 4,515,565 A * | 5/1985 | Winter-Moore et al. ...... 433/221 |
| 5,423,677 A * | 6/1995 | Brattesani ...................... 433/72 |
| 5,857,852 A * | 1/1999 | Garman ........................ 433/102 |
| 7,306,459 B1 * | 12/2007 | Williams et al. ................ 433/29 |
| 2003/0219694 A1 * | 11/2003 | Bianchetti et al. .............. 433/29 |
| 2003/0219699 A1 * | 11/2003 | Martin .......................... 433/164 |
| 2004/0224288 A1 * | 11/2004 | Bornstein .................... 433/224 |
| 2005/0003328 A1 * | 1/2005 | Karmaker et al. ............. 433/220 |
| 2005/0282102 A1 * | 12/2005 | Kert ............................... 433/29 |
| 2007/0072153 A1 * | 3/2007 | Gross et al. ................... 433/224 |
| 2007/0260231 A1 * | 11/2007 | Rose et al. ...................... 606/13 |

* cited by examiner

*Primary Examiner* — Todd Manahan
*Assistant Examiner* — Yogesh Patel

(57) ABSTRACT

A handset includes a high power LED and a vibrator. An optical tip includes a stepwise tapered portion for insertion into a root canal. The optical tip is used in combination with the vibrator for distributing a photosynthesizer in a root canal. The optical tip is used in combination with the LED for activating the photosynthesizer.

7 Claims, 6 Drawing Sheets

HANDSET AND OPTICAL TIP FOR PHOTOSYNTHESIS

This application is a continuation in part of U.S. application Ser. No. 11/694,475 filed Mar. 30, 2007.

FIELD OF THE INVENTIONS

The present invention is in the field of medical devices and methods used by dental professionals. In particular, the present invention relates to devices and methods for disinfecting dentine material, such as in an endodontically prepared root canal, especially by means of a photosynthesizer.

BACKGROUND OF THE INVENTIONS

Root canals are prepared endodontically by removing the nerve and pulp for subsequent obturation with an appropriate obturator. Before the obturation step, the root canal must be disinfected to reduce the risk of post treatment infection.

WO 00/74587 discloses a device for photosynthesizing a root canal. In use, the endodontically prepared canal is filled with a photosynthesizer solution such as toluidine blue dye in an aqueous solution. On contact with the bacteria, the dye or other photosynthesizer conjugates with the bacteria. Next, a conventional root canal file that is mounted on a dental hand piece is placed in the photosynthesizer solution filled root canal and the file is rotated in the root canal so as to distribute the photosynthesizer solution throughout the root canal. The photosynthesizer solution is absorbed by bacteria in the root canal and releases $O^-$ (singlet oxygen) when exposed to light with a given wavelength which is specific to the absorption of each photosynthesizer. $O^-$ is highly poisonous for bacteria. Thereafter, an optical fiber with a special spherical tip is placed in the root canal. The optical fiber does not have a reflective layer along its length. The size of the spherical tip is such that the optical fiber can enter about ⅔ of the length of the root canal, i.e. the tip of the optical fiber cannot reach the apex of the root canal. The optical fiber is connected to a laser unit containing a conventional laser. The light generated by the laser is thus applied to the interior of the root canal to photoactivate the photosynthesizer solution. Thus, the photosynthesizer solution releases $O^-$ resulting in the death of the bacteria in the root canal. Thereafter the root canal is dried and the actual obturation process begins.

There are several disadvantages associated with this known device. The process requires the use of a handset and file as well as the laser unit with the optical tip. The dental practitioner needs to swap devices during the procedure thereby complicating and prolonging the procedure. This known method uses a relatively expensive and sensitive laser unit. Further, the spherical optical tip cannot reach down to the apex of the root canal and thus the efficiency of the light exposure of the apex and the portion of the root canal near the apex cannot be guaranteed. Also, the size of the spherical tip has to match the size of the endodontically prepared root canal. The size of the root canal depends on the anatomy of the tooth concerned and the size and shape of the root canals that have been used to prepare the canal. Consequently, the dental practitioner needs to have a variety of different sized light guides in stock, thereby increasing costs and complexity of the disinfection procedure.

Caries affected teeth are prepared by excavating bacteria infested dentine material. Conventionally the excavation is performed very thoroughly to ensure that the remaining dentine material is not infected. Thus, the excavation is often performed more extensively than strictly required from a "constructional" point of view due to the risk of subsequent infection.

SUMMARY

The inventions described below provide a optical tip for use in a root canal with a distal part that distributes light for photo activation of a photosynthesizer in the root canal.

The inventions described provide for a handset including an LED light and a vibrator that can be operably coupled to a optical tip.

The inventions described below also provide for a method of disinfecting a root canal by mechanical and optical action.

DETAILED DESCRIPTION OF THE INVENTIONS

Figure 1:
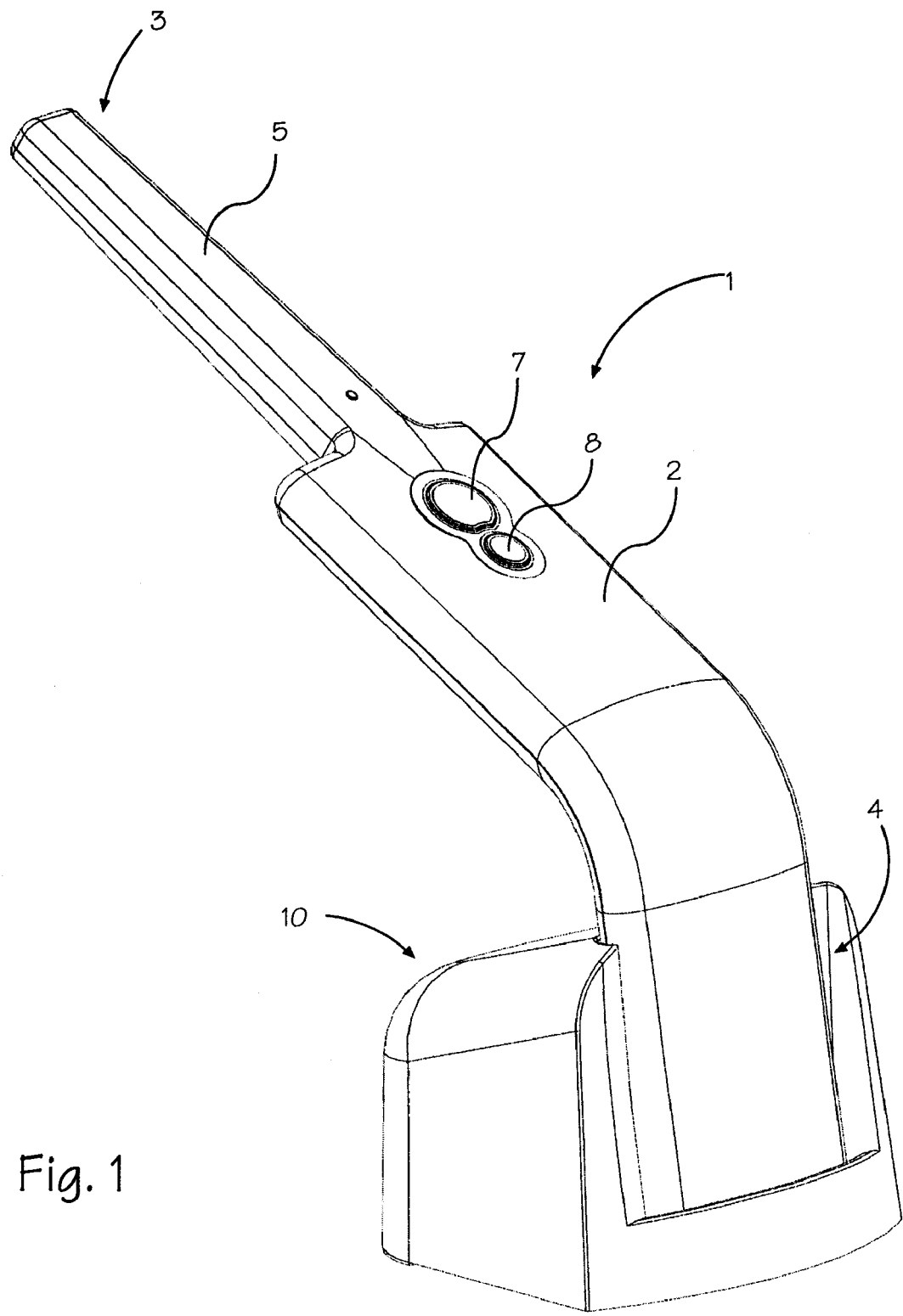
FIG. 1 is an elevated view of an embodiment of the handset according to the invention.

Reference will be made first to FIG. 1, which is an elevated view of a device for use by a dental professional for disinfecting a root canal. The device comprises a handset 1 and a base 10 on which the handset 1 can be placed when the handset 1 is not in use.

The handset includes a housing 2 and has a distal end 3 and a proximal end 4. The proximal end 3 is provided with a user exchangeable cover 5. The user exchangeable cover 5 is secured to the housing 2 by a snap action or the like. The exchangeable cover 5 is made from a disposable material or from a material that can be auto-enclaved repetitively. An example of material that can be auto-enclaved repetitively is Grilamid® TR FE 5599.

An activation/deactivation button 7 and an activation/deactivation button 8 are placed in the central portion of the housing 2.

Figure 2:
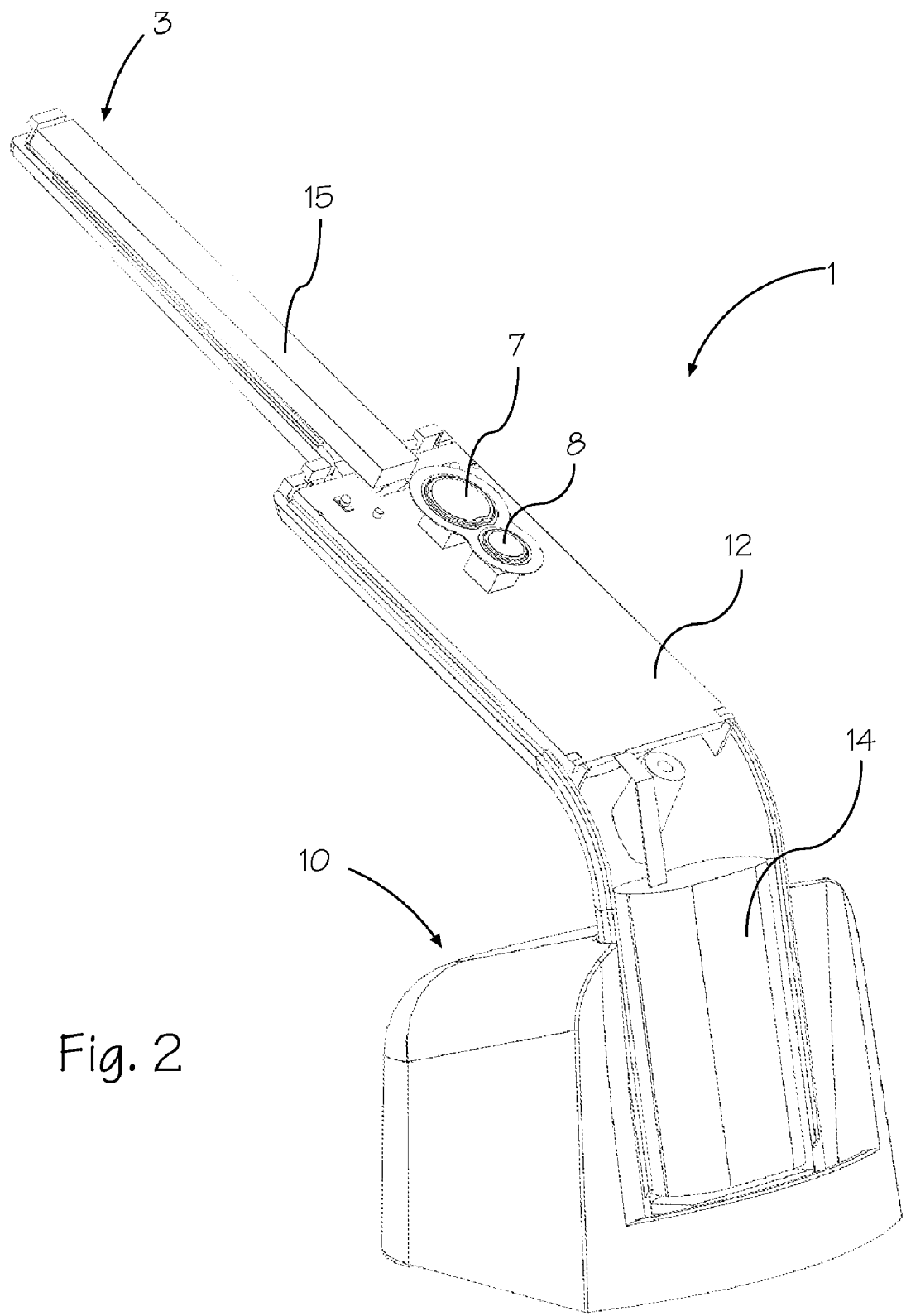
FIG. 2 is a cut open view of the handset shown in FIG. 1.
Figure 3:
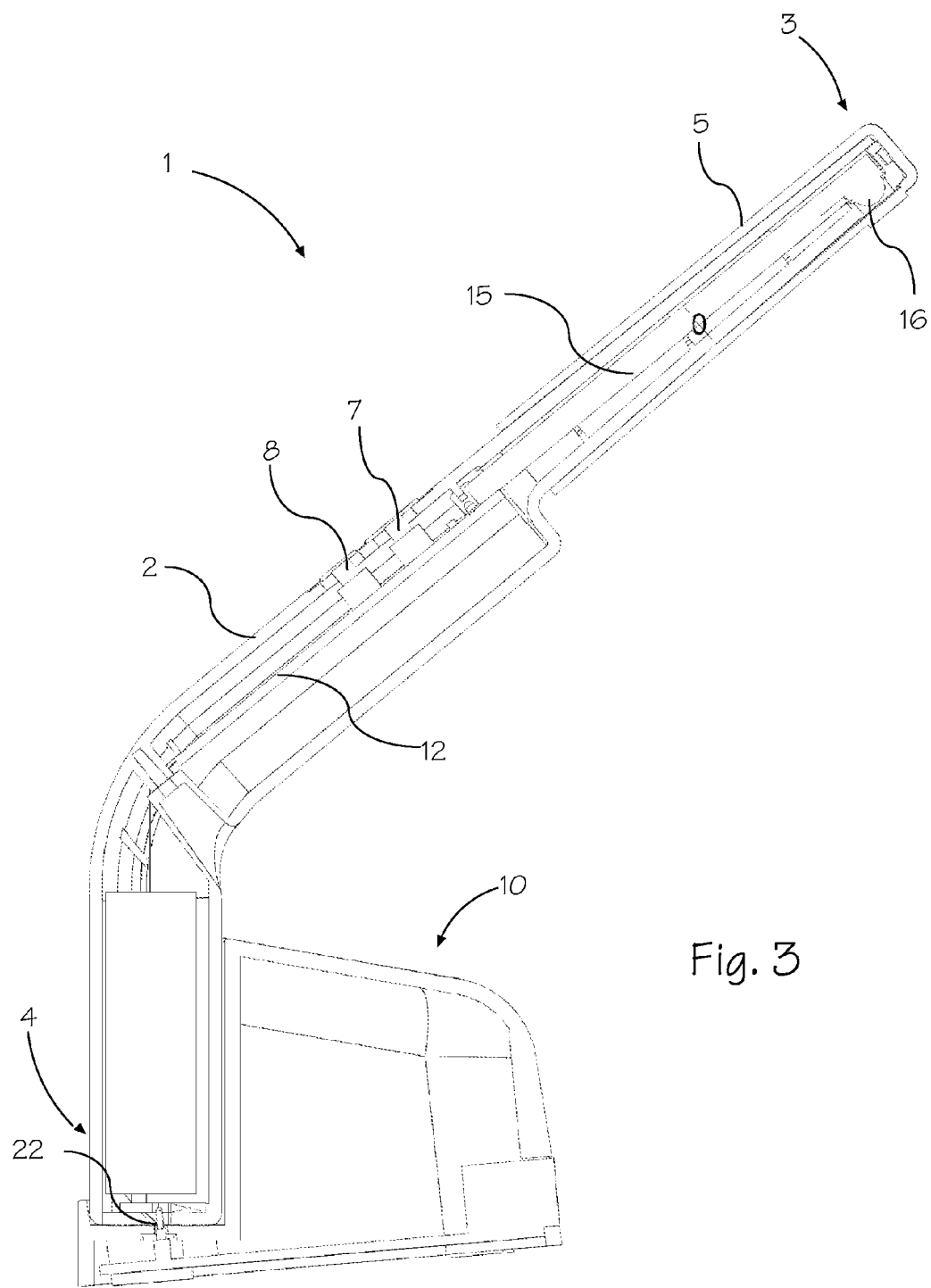
FIG. 3 is a sectional view of the handset shown in FIG. 1.

FIGS. 2 and 3 show some of the interior components of the handset 1 (not all components have been illustrated). A printed wired board 12 carries most of the electronic components (not all electronic components shown). Amongst these electronic components are a vibrator and a microprocessor (not shown).

The vibrator can be a vibrator motor that includes an electric motor that is provided with an eccentric weight (mass) on the drive shaft.

Figure 5:
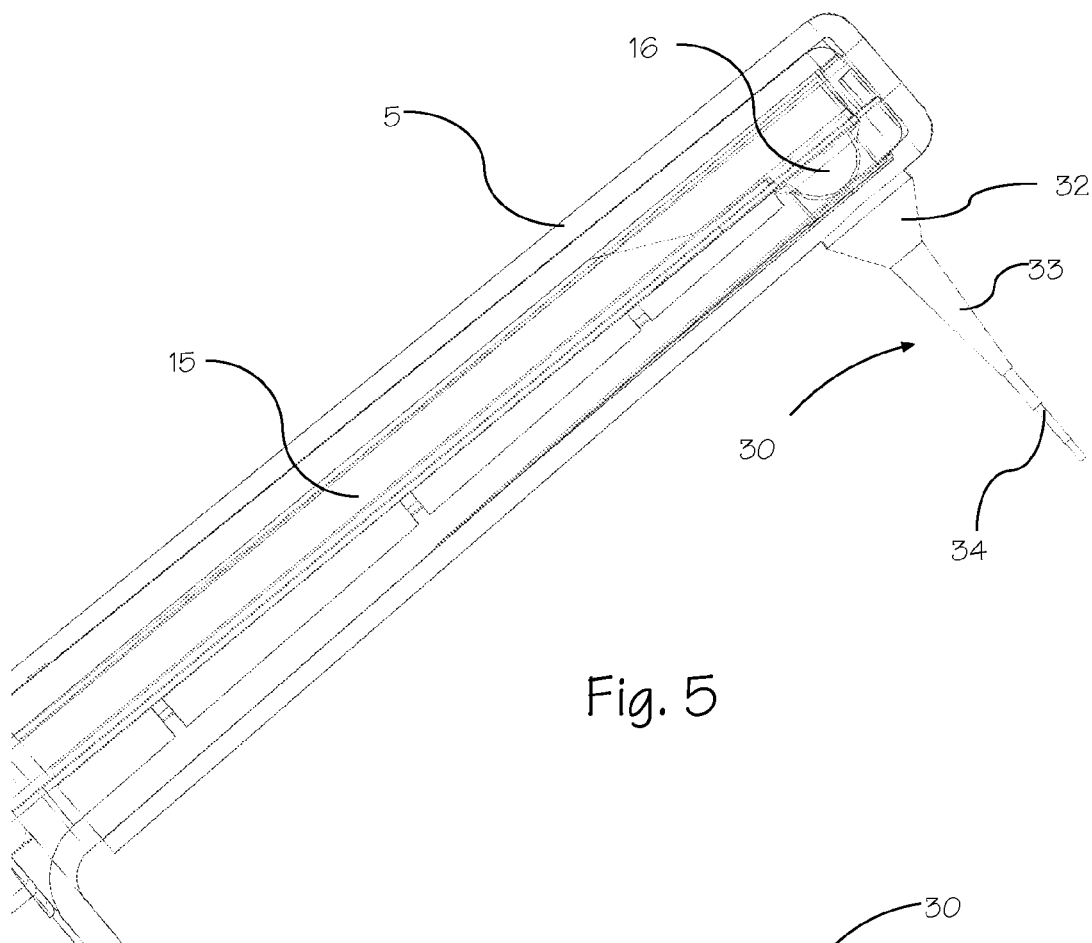
FIG. 5 is a detailed enlargement of the distal end of a handset as shown in FIG. 3 with a optical tip according to an embodiment of the invention coupled thereto.

The micro processor (not shown) controls the operation of the handset 1. The activation/deactivation button 7 and the activation/deactivation button 8 are a part of two switches that are also carried by the printed wired board 12. The printed wired board 12 is connected to a rechargeable battery 14. The battery is preferably of the lithium-ion polymer type. An arm 15 carries at its distal end an LED 16 with a high optical output. The optical output of the LED is preferably above 1 W. A suitable LED is type nr. LE-015015R1G manufactured by LedEngin, Inc. This LED consumes approximately 15 W power and emits more than 1 W optical power, typically approximately 2 W (red light, peak frequency of approximately 625-640 nm). The spherical tip of the LED 16 is used as a spherical coupling surface 28 (FIG. 5).

The handset 1 is electrically coupled at its proximal end 4 to the base 10 by contacts 22 for recharging the battery 14. The base 10 can be connected to the mains.

Figure 4:
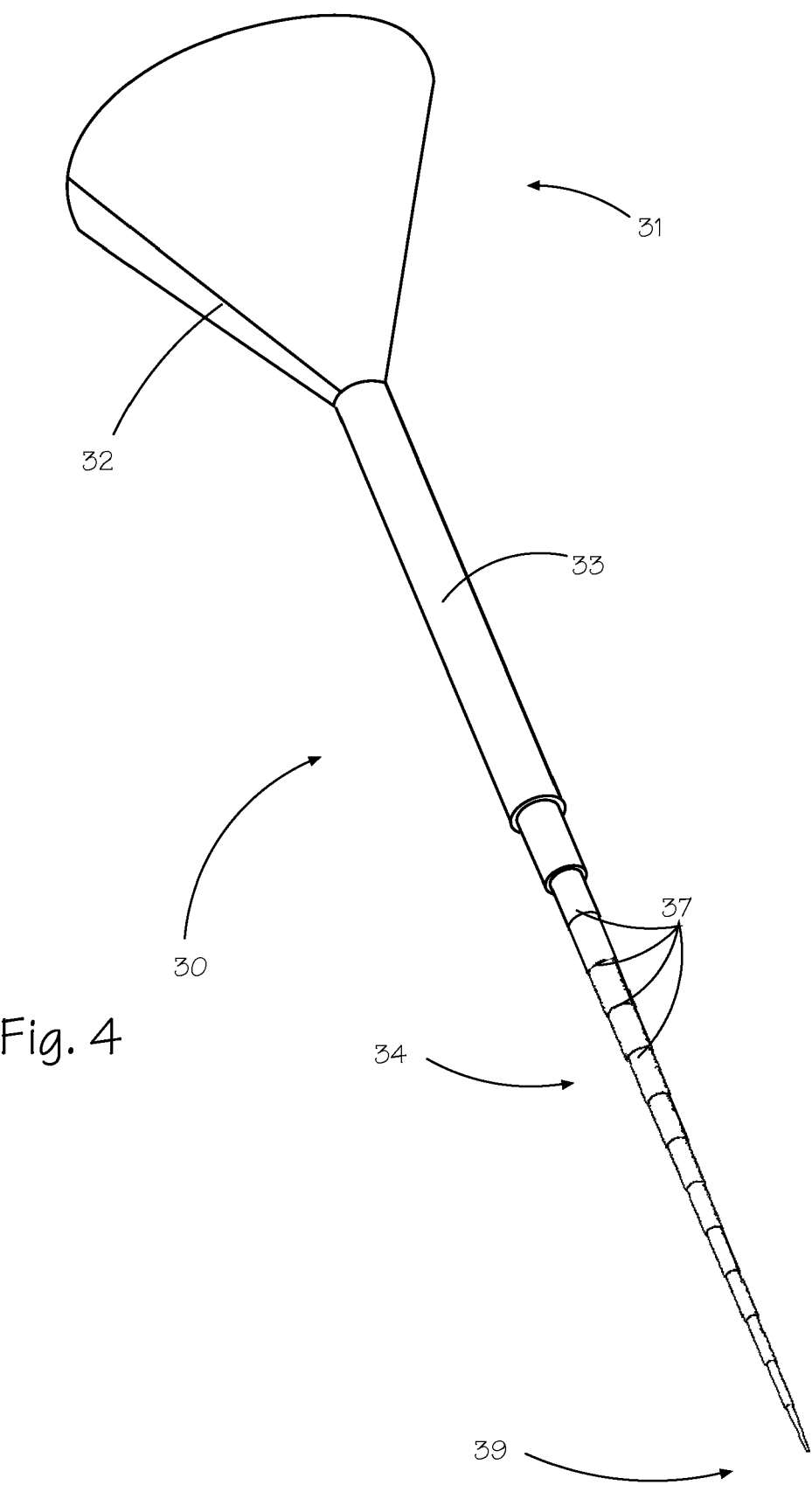
FIG. 4 is an elevated view of a optical tip according to an embodiment of the invention.

The handset 1 is used in combination with an optical tip 30, that can be operably coupled to the handset 1. As shown in FIG. 4, the optical tip 30 is an optical fiber for use in a root canal of a tooth (not shown), such as a human tooth, to which access has been gained. The optical tip 30 is made from a material with suitable optical characteristics for light guides, such as various resins, plastics or combinations thereof.

The optical tip 30 includes a proximal part 31, an intermediate part 33 and a distal part 34. The distal part 34 is shaped and dimensioned for introduction into the root canal. The distal part 34 tapers stepwise towards the distal end of the optical tip 30. The steps in the stepwise tapering portion form light emitting surfaces. Since the steps are distributed over the length of the tapered portion, the light entering the optical tip 30 is distributed along the length of the root canal into which the optical tip 30 is introduced.

The stepwise tapering portion includes a plurality of substantially cylindrical sections 37 between the steps.

The optical tip 30 is shaped and dimensioned to enter an endodontically prepared root canal with the distal end substantially reaching the apex of the endodontically prepared root canal. Due to natural variations in the size and shape of root canals, it is necessary to adapt the diameter of the distal portion 34 to the root canal in the tooth to be treated. For this purpose, a part of the stepwise tapered portion is severable with a hand tool. In particular, the diameter of the distal end of the optical tip 30 is adapted to the diameter of the apex of the endodontically prepared root canal by shortening it. Thus, a shorter tapered portion obtained by severing a distal part of the optical tip 30 provides for a larger diameter.

A dental practitioner will under normal circumstances keep various types of optical tips 30 in stock with varying degrees of average taper, such as optical tips with an average of 2°, 4° and 6° degrees taper.

The intermediate part 33 can be tapered or not tapered and serves to connect the proximal part 32 to the distal part 34.

The proximal part 32 is substantially shaped like a conical frustum, and is strongly tapered to create a substantial contact or coupling surface at the proximal end of the optical tip 30. The proximal end of the optical tip 30 is connectable proximally to a source of light, in particular to the out coupling surface 28 of the LED 16. Further, the proximal end is connectable proximally to a source of mechanical vibration.

FIG. 5 shows the distal portion 7 of the handset in detail with an optical tip 30 attached thereto. The end of the arm 15 is provided with the LED 16 with the coupling surface 28. The user exchangeable cover 5 is provided with a recess in which a portion of the optical tip 30 can be received and secured. The coupling surface 28 is, in the shown embodiment, convex with a concave counterpart (coupling surface) 38 on the proximal end of the optical tip 30. However, in another embodiment (not shown), the arrangement can be reversed with a concave coupling surface 28 on the LED 16 and a convex coupling surface on the proximal end of the optical tip 30. In this embodiment the proximal end of the optical tip 30 includes a cylindrical projection for mechanical connection to the recess in the user exchangeable cover 5.

The optical coupling between the concave and convex surfaces allows for light emitted by the LED 16 to be guided into the optical tip 30. The mechanical coupling between the handset 1 and the optical tip allows for vibrations generated by the vibrator to be transmitted to the optical tip 30.

Figure 6:
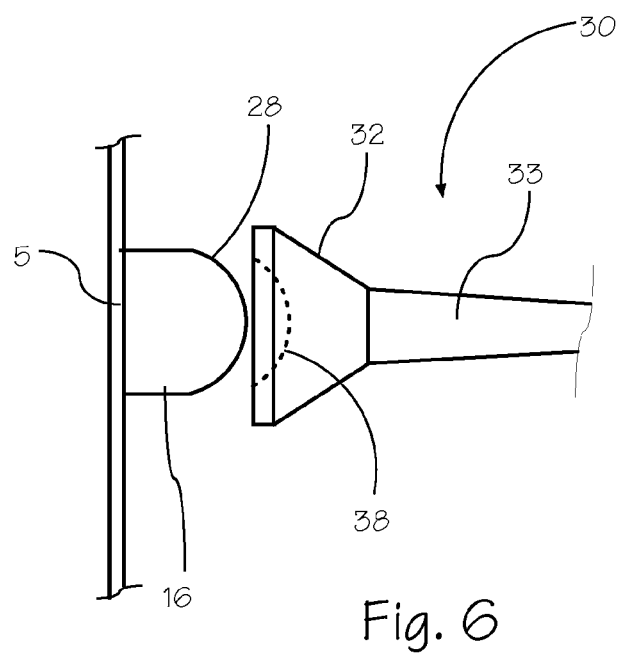
FIG. 6 illustrates another embodiment of the optical tip according to the invention and the corresponding coupling portion of the device according to an embodiment of the invention.

FIG. 6 shows another embodiment of the coupling between the optical tip 30 and the light guide 16 in the handset. In this embodiment the LED 16 protrudes from the user exchangeable cover 5 with its convex coupling surface 28. The proximal end of the optical tip 30 is provided with a concave coupling surface 38. In use, an operator places the convex coupling surface 28 of the LED 16 on the concave coupling surface of the optical tip 30 to create a mechanical and an optical coupling between the handset and the optical tip. The convex surface can mate with the concave surface over a range of angles in a fashion similar to that of a ball joint, thereby reducing the need to frictionally align the headset with the optical tip and thus facilitating the use in the relatively small oral cavity.

In a variation of this embodiment the concave and convex surfaces are exchanged, so that the LED 16 is provided with a concave coupling surface and the optical tip 30 is provided with a convex surface (not shown).

In order to perform a disinfection treatment to a root canal, a dental practitioner will gain access to the root canal and select an optical tip 30 with the appropriate average degree of taper. The length and diameter of the optical tip are adapted as required by severing a distal portion from the optical tip 30. Thereafter, a liquid synthesizer is filled into the root canal. A suitable photosynthesizer known is Toluidine Blue (ortho-toluidine), but other photosynthesizers can be used.

When a handset 1 and optical tip 30 as described with reference to FIG. 6 are used, the next step is introducing the tapered portion of the optical tip 30 into the root canal with the distal part 34 of the optical tip 30 protruding from the root canal. Thereafter, the dental practitioner takes the handset 1 and places the coupling surface 28 of the LED 16 on the coupling surface 38 of the optical tip 30. Then, the dental practitioner activates the vibrator by pressing on the button 7. In an embodiment, the duration of the activation of the vibrator is determined by the processor in the handset for a preprogrammed period of time. The predetermined period of time is selected in order to ensure that the photosynthesizer in the root canal is properly distributed in the root canal by the effect of the vibrating optical tip 30. In another embodiment, the dental practitioner presses button 7 again after a given period of time that is sufficient for properly distributing the photosynthesizer in the root canal.

Next, the dental practitioner activates the LED in the handset 1 for activating the photosynthesizer in the root canal to thereby kill bacteria in the root canal. The length of the activation of the LED is in an embodiment determined by the processor in the handset 1. The length of the activation of the LED 16 is determined by the processor to a length that is sufficient for properly activating the photosynthesizer. In another embodiment the duration of the activation of the LED 16 is manually determined by the dental practitioner who will press button 8 to deactivate the LED 16. Alternatively, the dental practitioner can simply take the handset 1 away from the optical tip 30.

The wavelength of the light emitted by the LED 16 in the handset 1 depends on the absorption spectra of the photo synthesizer used.

The procedure is essentially the same when a handset 1 and optical tip 30 according to the embodiment illustrated with reference to FIG. 5 are used. However, in this case the optical tip 30 is secured and coupled to the handset 1 before introduction into the root canal. Thus, the optical tip 30 is in this embodiment inserted into the root canal whilst the optical tip is secured to the handset 1.

After disinfection of the root canal, it is flushed and dried. The dental practitioner may proceed with obturating the root canal.

Figure 7:
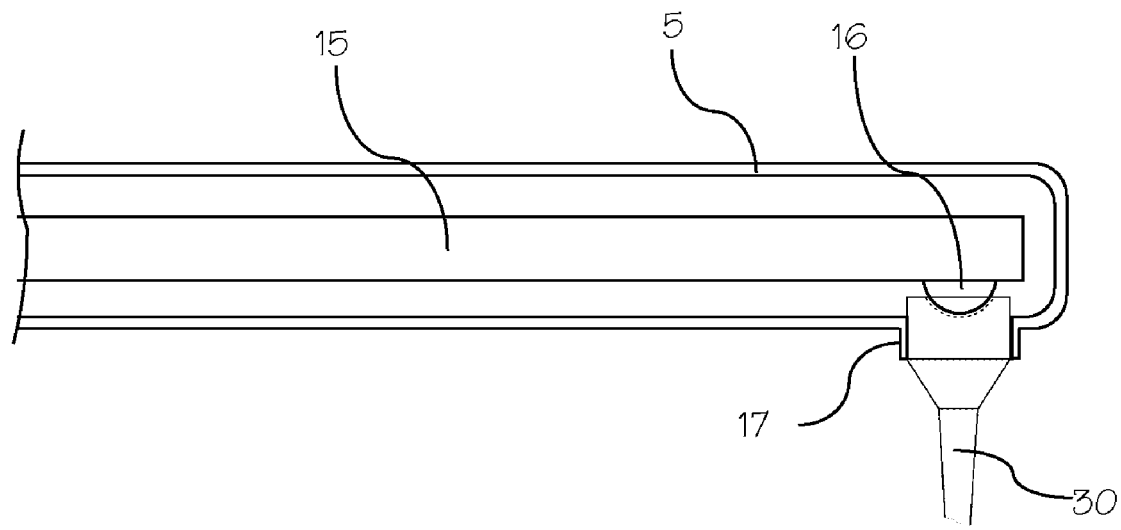
FIG. 7 is a detailed enlargement of the distal end of another embodiment of the handset with an optical tip according to an embodiment of the invention coupled thereto.

FIG. 7 illustrates the distal end of another embodiment of the handset 1. This embodiment is essentially identical to the ones described above, except that the user exchangeable cover 5 is provided with a collar 17. The proximal end of the optical tip 30 fits snugly into the opening defined by the collar 17. The snug fit ensures that the optical tip is secured to the cover 5.

Figure 8:
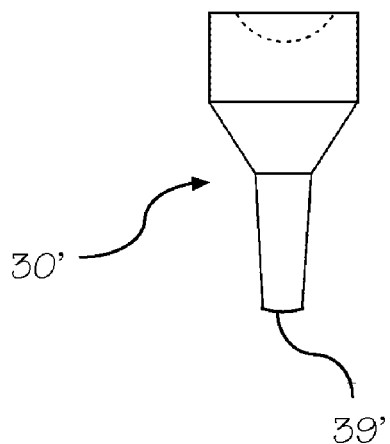
FIG. 8 is another embodiment of the optical tip according to the invention.

FIG. 8 illustrates another embodiment of the optical tip. The optical tip 30' according to this embodiment is provided with a blunt distal end that can be used for directing light to a targeted area.

According to an embodiment of the invention, a caries infected area of the tooth is excavated less intensively than in a conventional method. Dentine material is only removed as far as it has weakened and is heavily infected with bacteria. Dentine material that it is only slightly infected but not weakened is not removed. A liquid photosynthesizer is applied to the excavated area of the tooth. In the following step, the dental practitioner brings the tip of a blunt optical tip, such as the light guide illustrated in FIG. 8, in close proximity to be excavated area of the tooth. The optical tip 30' is attached to a handset 1 as described above and, by activating the light in the handset, the photosynthesizer material in the excavated area of the tooth is activated and thereby any remaining bacteria are killed. After this step, the excavated area is flushed and dried, so that the following tooth reconstruction procedure may commence in accordance with any conventional method.

According to another embodiment of the invention, gingivitis is being treated by applying a liquid photosynthesizer to the pockets between the gums and the teeth. Any conventional method for applying liquid in these pockets, as known for other treatments of gingivitis, can be used. In the next step, intense light with a wavelength suitable for the activation of the photosynthesizer is applied to the photosynthesizer through the gums. A blunt optical tip as shown in FIG. 8 can be used for this purpose. The gums are transparent to light and only the blood in the gums hinders the light in reaching the photosynthesizer. With a sufficiently high intensity of the light leaving the optical tip, enough light passes through the gums for activating the photosynthesizer to thereby kill any bacteria that are disposed between the gums and teeth. A handset 1 as described above in combination with a blunt optical tip 30' described above can be used for applying the high intensity light.

The invention has numerous advantages. Different embodiments or implementations may yield one or more of the following advantages. It should be noted that this is not an exhaustive list and there may be other advantages which are not described herein. One advantage of the invention is that it allows for effective distribution and activation of a photosynthesizer with few steps and with one and the same tool. Another advantage of the invention is that it provides for a flexible coupling between an optical tip and a handset. A further advantage of the invention is that it provides for an optical tip that effectively distributes the emitted light along the length of a root canal. Yet another advantage of the invention is that it provides for an optical tip that can easily be adapted to the diameter of the root canal. A further advantage of the invention is that it allows for the use of an LED as the source of light for disinfection with a photosynthesizer. Another advantage of the invention is that it allows for a reduced excavation of caries affected teeth. Yet another advantage of the invention is that it provides for an effective method for killing bacteria that are residing between the gums and the teeth.

The term "comprising" as used in the claims does not exclude other elements or steps. The term "a" or "an" as used in the claims does not exclude a plurality.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon. Moreover, it should be appreciated that those skilled in the art, upon consideration of the present disclosure, may make modifications and/or improvements on the apparatus hereof and yet remain within the scope and spirit hereof as set forth in the following claims.

The invention claimed is:

1. A device for disinfecting an endodontically prepared root canal of a tooth, said device comprising:
    a handset provided inside with an LED and a vibrator;
    an optical tip shaped and dimensioned for introduction into said root canal, said optical tip having a proximal and a distal end wherein at least a portion of the length of the optical tip including the distal end tapers stepwise towards the distal end of the optical tip for introduction into said root canal, wherein said stepwise tapering portion forms light emitting surfaces and being configured to spread light around and along the root canal, and
    said optical tip being connected to said handset for operably connecting said LED to said optical tip and for transmitting vibrations from said vibrator to said optical tip.

2. A device according to claim 1, wherein the LED has an optical output of more than 1 W.

3. A device according to claim 1, further including a rechargeable lithium-ion polymer battery.

4. A device according to claim 3, wherein said optical tip has a distal end for introduction into the root canal and a proximal end that is provided with a convex coupling surface.

5. A device according to claim 4, wherein said hand piece is provided with a light guide operably connected to said LED, said light guide being provided with a concave coupling contact surface for establishing an operable connection with the proximal end of said optical tip.

6. A device according to claim 3, wherein said optical tip has a distal end for introduction into the root canal and a proximal end that is provided with a concave coupling surface.

7. A device according to claim 6, wherein said hand piece is provided with a light guide operably connected to said LED, said light guide being provided with a convex coupling contact surface for establishing an operable connection with the proximal end of said optical tip.

* * * * *